US012318348B2

(12) United States Patent
Swoboda et al.

(10) Patent No.: US 12,318,348 B2
(45) Date of Patent: Jun. 3, 2025

(54) ON AMBULATORY RESPIRATORY ASSIST DEVICE

(71) Applicant: The Trustees of the University of Pennsylvania, Philadelphia, PA (US)

(72) Inventors: Marek Swoboda, Philadelphia, PA (US); Michal Swoboda, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 852 days.

(21) Appl. No.: 17/413,740

(22) PCT Filed: Dec. 16, 2019

(86) PCT No.: PCT/US2019/066603
§ 371 (c)(1),
(2) Date: Jun. 14, 2021

(87) PCT Pub. No.: WO2020/131736
PCT Pub. Date: Jun. 25, 2020

(65) Prior Publication Data
US 2022/0054353 A1 Feb. 24, 2022

Related U.S. Application Data

(60) Provisional application No. 62/780,608, filed on Dec. 17, 2018.

(51) Int. Cl.
*A61H 31/00* (2006.01)
*A61H 31/02* (2006.01)
(52) U.S. Cl.
CPC ....... *A61H 31/02* (2013.01); *A61H 2201/107* (2013.01); *A61H 2201/1238* (2013.01);
(Continued)

(58) Field of Classification Search
CPC ................... A61H 31/00; A61H 31/02; A61H 2201/1619; A61H 2201/165;
(Continued)

(56) References Cited

U.S. PATENT DOCUMENTS 1,834,580 A 12/1931 Drinker et al.
2,065,982 A 12/1936 Nordin
(Continued)

FOREIGN PATENT DOCUMENTS

FR 1051708 1/1954
WO WO-2005039679 A1 * 5/2005 ............. A61H 31/02
WO WO-2017165359 A1 * 9/2017 ......... A61H 23/0245

OTHER PUBLICATIONS

International Search Report and Written Opinion of the International Searching Authority issued for International PCT Application No. PCT/US2019/066603 on Mar. 3, 2020.

*Primary Examiner* — Brandy S Lee
*Assistant Examiner* — Savannah L Gabriel
(74) *Attorney, Agent, or Firm* — Howson & Howson LLP

(57) ABSTRACT

Provided herein is a device comprising a cuirass, which includes a shell, at least one sensor, a pressure creation means for providing at least one of a negative pressure or a positive pressure within the shell, and a controller operably connected to the pressure creation means, wherein the controller is adapted to receive an input signal from the at least one sensor and adapted to provide an output signal to the pressure creation means, and wherein the pressure creation means is adapted to provide a greater or lesser amount of pressure within the shell in response to the output signal. Also provided are methods of use.

18 Claims, 14 Drawing Sheets

(52) U.S. Cl.
CPC ............... *A61H 2201/1621* (2013.01); *A61H 2201/1652* (2013.01); *A61H 2201/5023* (2013.01); *A61H 2201/5071* (2013.01); *A61H 2201/5082* (2013.01); *A61H 2201/5084* (2013.01); *A61H 2201/5087* (2013.01); *A61H 2230/405* (2013.01)

(58) Field of Classification Search
CPC ........ A61H 2201/506; A61M 16/0075; A61M 16/0078; A61M 16/0081; A61M 16/0084; G01F 23/263
See application file for complete search history.

(56) References Cited

U.S. PATENT DOCUMENTS

| | | | | |
|---|---|---|---|---|
| 2,079,952 | A | 5/1937 | Sahlin | |
| 2,287,939 | A | 6/1942 | Kraft | |
| 2,309,361 | A | 1/1943 | Terhaar | |
| 2,456,724 | A | 12/1948 | Mullikin | |
| 2,466,108 | A | 4/1949 | Huxley, III | |
| 2,480,980 | A | 9/1949 | Terhaar | |
| 2,529,258 | A | 11/1950 | Lobo | |
| 2,572,787 | A * | 10/1951 | Wallin | A61H 31/02 601/43 |
| 2,629,372 | A | 2/1953 | Wallin | |
| 2,825,327 | A | 11/1954 | Tunnicliffe | |
| 2,699,163 | A | 1/1955 | Engstrom | |
| 2,759,474 | A * | 8/1956 | Kling | A61H 31/02 601/44 |
| 3,078,842 | A * | 2/1963 | Gray | A61H 31/00 601/44 |
| 3,368,550 | A | 2/1968 | Glascock | |
| 3,961,626 | A * | 6/1976 | Houchen | A62B 7/00 128/201.27 |
| 4,257,407 | A * | 3/1981 | Macchi | A61H 31/02 601/44 |
| 4,784,130 | A * | 11/1988 | Kenyon | A61M 16/0677 128/204.26 |
| 4,844,390 | A | 7/1989 | Duke | |
| 4,881,527 | A | 11/1989 | Lerman | |
| 4,945,899 | A * | 8/1990 | Sugiyama | A61H 31/02 600/534 |
| 4,971,042 | A | 11/1990 | Lerman | |
| 5,076,259 | A | 12/1991 | Hayek | |
| 5,222,491 | A | 6/1993 | Thomas | |
| 5,573,498 | A | 11/1996 | Hayek | |
| 5,820,572 | A | 10/1998 | Palmer | |
| 6,345,618 | B1 | 2/2002 | Hayek | |
| 6,488,641 | B2 | 12/2002 | Hansen | |
| 6,910,479 | B1 | 6/2005 | Van Brunt | |
| 8,202,237 | B2 | 6/2012 | Helgeson et al. | |
| 10,105,281 | B1 | 10/2018 | Costella | |
| 2002/0078958 | A1 | 6/2002 | Stenzler | |
| 2007/0235030 | A1* | 10/2007 | Teetzel | A62B 9/04 128/205.12 |
| 2007/0276299 | A1 | 11/2007 | Jiang et al. | |
| 2008/0000477 | A1 | 1/2008 | Huster et al. | |
| 2008/0115786 | A1 | 5/2008 | Sinderby et al. | |
| 2008/0149099 | A1* | 6/2008 | Doyle | A61H 31/02 128/204.21 |
| 2008/0167586 | A1* | 7/2008 | Baldauf | A61H 31/02 601/44 |
| 2009/0171256 | A1 | 7/2009 | Fiorina | |
| 2011/0098741 | A1 | 4/2011 | Pfeiffer | |
| 2012/0174275 | A1 | 7/2012 | Carlson | |
| 2013/0324894 | A1* | 12/2013 | Herken | A61H 31/006 601/41 |
| 2014/0113753 | A1 | 4/2014 | Craig | |
| 2015/0045704 | A1 | 2/2015 | Lurie et al. | |
| 2016/0324722 | A1* | 11/2016 | Sinderby | A61H 9/0078 |
| 2016/0349738 | A1 | 12/2016 | Sisk | |
| 2017/0100550 | A1* | 4/2017 | Van De Laar | A61M 15/0021 |
| 2017/0209334 | A1 | 7/2017 | Francois et al. | |
| 2017/0304147 | A1* | 10/2017 | Glenn | A61H 35/04 |
| 2019/0029920 | A1* | 1/2019 | Kostic | A61G 1/048 |
| 2020/0054830 | A1* | 2/2020 | Schabbach | A61M 5/31533 |

* cited by examiner

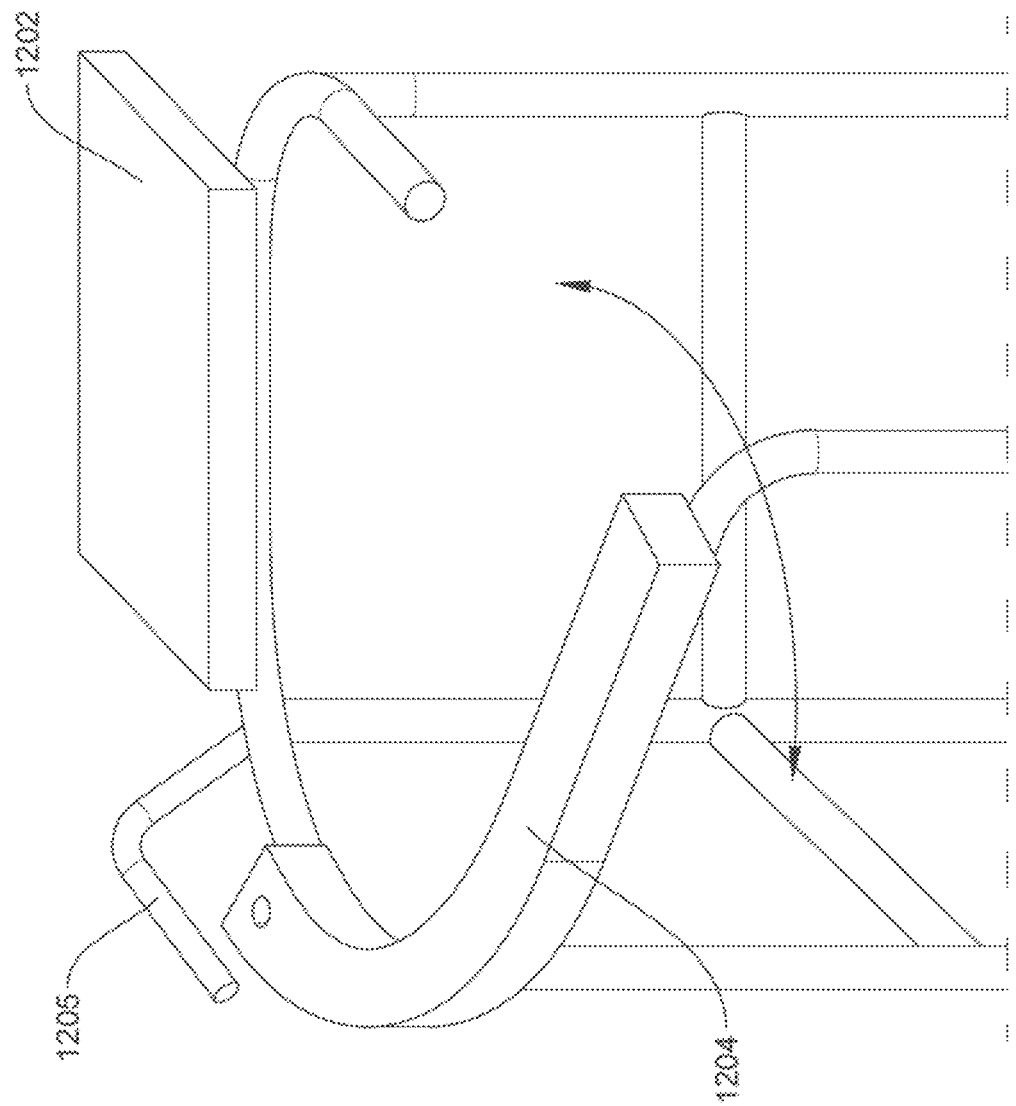

ON AMBULATORY RESPIRATORY ASSIST DEVICE

FIELD OF THE INVENTION

The invention relates to medical devices, and particularly to devices for the treatment of dyspnea on exertion (DOE), as found in chronic obstructive pulmonary disease (COPD) and other respiratory disorders.

BACKGROUND OF THE INVENTION

COPD is an obstructive lung disease that affects 15 million Americans each year. Of these, approximately twenty percent suffer from severe DOE that drastically limits their daily activities. COPD patients experience DOE for a variety of reasons, with smoking as the primary cause. Most cases of COPD can be prevented by reducing exposure to risk factors, and while the disease remains one that may be treated, no cure is currently known.

To combat DOE in COPD and other respiratory disorders, the most important goals are to help the patient breathe out faster in order to prevent dynamic hyperinflation and to offload the work of the respiratory muscles. Historically, COPD was treated with supplemental oxygen, various therapeutics such as bronchodilators or corticosteroids, and other surgical procedures. In certain instances, devices that assist in clearing mucous from the air pathways have proven to be somewhat effective. Unfortunately, none of these treatment options provide a universal approach for all patients, and thus those with COPD often continue to suffer despite treatment.

Herein is described a new approach towards treating COPD, namely a device that addresses DOE limitations and assists in breathing, an apparatus that will be referred to as a "cuirass/ventilator," a "cuirass/ventilator apparatus," or a "cuirass/ventilator combination," which is an apparatus having a cuirass and a ventilator.

SUMMARY OF THE INVENTION

The various embodiments described herein include devices comprising a cuirass that is adapted to engage to a patient and, through the application of certain pressure applications to the cuirass, improves breathing for COPD patients, though the devices could assist additional patients having certain lung function issues, as devices aid in breathing.

In certain embodiments, provided herein is a device including a cuirass, at least one sensor, a pressure creation means for providing at least one of a negative pressure or a positive pressure within the shell, and a controller operably connected to the pressure creation means. The cuirass includes a shell. The controller is adapted to receive an input signal from the at least one sensor and adapted to provide an output signal to the pressure creation means. The pressure creation means is adapted to provide a greater or lesser amount of pressure within the shell in response to the output signal.

In certain embodiments, provided herein is a device including a cuirass, said cuirass including a shell, at least one sensor, a pressure creation means for providing at least one of a negative pressure or a positive pressure within the shell, and a controller operably connected to the pressure creation means. The sensor is adapted to measure a breath pattern parameter corresponding to a patient's breathing pattern. The controller is adapted to receive a breathing pattern input signal from the at least one sensor and to calculate a predicted breath time. The predicted breath time is a time at which at least one of a future inhalation or a future exhalation of the patient will take place. The controller is adapted to compare the breathing pattern input signal from the at least one sensor to the predicted breath time. The controller is adapted to modify the predicted breath time if the breathing pattern input signal and the predicted breath time differ by a pre-determined threshold. The controller provides an output signal corresponding to the predicted breath time to the pressure creation means.

In certain embodiments, provided herein is a device including a cuirass including a shell, at least one sensor, a pressure creation means for providing at least one of a negative pressure or a positive pressure within the shell, and a controller operably connected to the sensor. The sensor is adapted to measure a true breath-pattern parameter corresponding to a patient's breathing pattern. The sensor is adapted to measure a movement parameter corresponding to a movement of an extremity of the patient. The controller is adapted to receive a true breath input signal from the sensor corresponding to the patient's breathing pattern. The controller is adapted to receive a noise input signal from the sensor corresponding to the movement of an extremity of the patient. The controller is adapted to modify the true breath input signal if the noise input signal meets or exceeds a pre-determined threshold. The controller is adapted to provide an output signal to the pressure creation means. The pressure creation means is adapted to provide a greater or lesser amount of pressure within the shell in response to the output signal.

In some embodiments, at least one sensor is a harness-based sensor mechanically linked to the harness. In some embodiments, the harness-based sensor includes a first harness-based sensor and a second harness-based sensor. The first and second harness-based sensors are adapted to measure distance. The first harness-based sensor is adapted to measure the distance between the sensor and a patient's chest. The second harness sensor is adapted to measure the distance between the sensor and a patient's abdomen. The input signal includes signals from the first harness-based sensor and the second harness-based sensor. The output signal is dependent on at least the signals from the first harness-based sensor and the second harness-based sensor. In some embodiments, the harness-based sensor measures a physical quantity of the harness selected from the group consisting of: force, stress, and strain, and combinations thereof.

In some embodiments, the at least one sensor includes a first cuirass-based sensor and a second cuirass-based sensor mechanically linked to the cuirass. The first cuirass-based sensor is adapted to measure the distance between the cuirass-based sensor and a patient's chest. The second cuirass-based sensor is adapted to measure the distance between the cuirass-based sensor and a patient's abdomen. The input signal includes signals from the first cuirass-based sensor and the second cuirass-based sensor. The output signal is dependent on at least the signals from the first cuirass-based sensor and the second cuirass-based sensor.

In some embodiments, the cuirass further includes a pneumatic port mechanically linked to the pressure creation means, the at least one sensor is an airflow sensor, and the input signal includes a signal from the airflow sensor. The airflow sensor is adapted to measure airflow within the pneumatic port. The output signal is dependent on at least the signal from the airflow sensor.

In some embodiments, the at least one sensor is a pressure sensor and the input signal includes a signal from the pressure sensor. The output signal is dependent on at least the signal from the pressure sensor.

In some embodiments, the at least one sensor is selected from the group consisting of: an impedance plethysmography sensor, a microphone, an EMG sensor, and an ultrasound sensor, and combinations thereof. The input signal includes a signal from the at least one sensor selected from the group. The output signal is dependent on at least the signal from the at least one sensor selected from the group.

In some embodiments, the at least one sensor is a volume sensor and the input signal includes a signal from the volume sensor. The output signal is dependent on at least the signal from the volume sensor. In some embodiments, the volume sensor is a capacitive sensor including at least two electrodes and at least one of the at least two electrodes is a body-based sensor. The body-based sensor is adaptable to be placed in direct or indirect contact with an anterior portion of at least one of the chest or the abdomen of a patient. At least one of the at least two electrodes is a cuirass-based sensor. The cuirass-based sensor is in direct or indirect connection with the cuirass. The controller is operably connected to the at least two electrodes and adapted to receive an input signal comprising at least a signal from the body-based sensor and a signal from the cuirass-based sensor. The controller is adapted to calculate an interior volume of the cuirass based on data received through the input signal.

In some embodiments, the cuirass further includes a pneumatic port mechanically linked to the pressure creation means and the volume sensor being an airflow sensor. The airflow sensor is adapted to measure airflow within the pneumatic port. The controller is operably connected to the airflow sensor and adapted to receive an input signal comprising at least a signal from the airflow sensor. A physical dimension of at least a segment of the pneumatic port is known. The physical dimension is selected from the group consisting of: length, diameter, circumference, and volume, and combinations thereof. The controller is adapted calculate an interior volume of the cuirass based on the physical dimension and data received through the input signal. In some embodiments, the volume sensor includes at least a pressure sensor and a temperature sensor. The controller is operably connected to the airflow sensor and adapted to receive an input signal including at least a signal from the pressure sensor and a signal from the temperature sensor. The controller is adapted to calculate an approximate volume of a space defined by the anterior portion of at least one of the chest or the abdomen of the patient and the shell based on data received through the input signal.

In some embodiments, the controller is adapted to receive the breathing pattern input signal while the pressure creation means is providing at least one of the negative or the positive pressure. In some embodiments, the pressure provided by the pressure creation means is constant. In some embodiments, the pressure provided by the pressure creation means is varying.

In some embodiments, the controller is adapted to receive the breathing pattern input signal while the pressure creation means is not providing at least one of the negative pressure or the positive pressure.

In some embodiments, the controller is adapted to receive the breathing pattern input signal while the pressure creation means is providing at least one of the negative pressure or the positive pressure as well as when the pressure creation means is not providing at least one of the negative pressure or the positive pressure. In some embodiments, the at least one sensor that is adapted to measure the breath pattern parameter is the same at least one sensor that is adapted to measure the movement parameter.

In some embodiments, the device further includes at least two sensors. The at least one of the at least one sensor that is adapted to measure the breath pattern parameter is a different sensor than at least one of the at least one sensor that is adapted to measure the movement parameter. In some embodiments, the at least one of the at least one sensor that is adapted to measure the movement parameter is located exterior to the shell. In some embodiments, the at least one of the at least one sensor that is adapted to measure the movement parameter is located exterior to the shell is an accelerometer. In some embodiments, the device further includes a backpack. The backpack is shaped for engagement with an anterior portion of the back of a patient. The at least one of the at least one sensor that is adapted to measure the movement parameter is located exterior to the shell is located in the backpack. In some embodiments, the shell includes an interior face and an exterior face. The at least one sensor that is adapted to measure the movement parameter is a pressure sensor. The at least one sensor that is adapted to measure the movement is at least partially located an interior volume of the cuirass. The controller is adapted to calculate a pressure quality selected from the group consisting of: pressure gradient, pressure amplitude, pressure signal shape, and pressure signal frequency, and combinations thereof, based on data received through the input signal.

In certain embodiments, provided herein is a device including a cuirass including a shell, a manual interface, a pressure creation means for providing at least one of a negative pressure or a positive pressure within the shell, and a controller operably connected to the pressure creation means. The manual interface is adapted to allow a patient to manually modify at least one of a maximum pressure level within the cuirass or a maximum rate of change over time of pressure within the cuirass. The controller is adapted to receive an input signal from the manual interface and adapted to provide an output signal to the pressure creation means. The pressure creation means is adapted to provide a greater or lesser amount of pressure within the shell in response to the output signal.

In certain embodiments, provided herein is a device including a cuirass comprising a shell, a ventilator adapted to be worn over a patient's mouth, at least one sensor, a cuirass pressure creation means for providing at least one of a first negative pressure or a first positive pressure within the shell, a ventilator pressure creation means for providing at least one of a second negative pressure or a second positive pressure within the ventilator, and a controller operably connected to the cuirass pressure creation means and the ventilator pressure creation means. The controller is adapted to receive an input signal from the at least one sensor and adapted to provide a cuirass output signal to the cuirass pressure creation means. The cuirass pressure creation means is adapted to provide a greater or lesser amount of pressure within the shell in response to the cuirass output signal. The ventilator pressure creation means is adapted to provide a greater or lesser amount of pressure within the ventilator in response to the ventilator output signal. The ventilator pressure creation means is adapted to provide a second positive pressure when the cuirass pressure creation means provides a first negative pressure.

In certain embodiments, provided herein is a device including a cuirass including a shell, a backpack, a harness mechanically linked to the backpack and the cuirass, a docking stand, a pressure creation means for providing at least one of a negative pressure or a positive pressure within the shell, and a controller operably connected to the pressure creation means. The pressure creation means is adapted to provide a greater or lesser amount of pressure within the shell in response to an output signal provided by the controller. At least one of the cuirass, the harness, or the backpack comprises a docking catch mechanism. The docking catch mechanism is adapted to provide a temporary mechanical linkage between the docking stand and the at least one of the cuirass, the harness, or the backpack.

In certain embodiments, provided herein is a device including a cuirass including a shell which is surrounded by a border shaped for engagement with an anterior portion of at least one of a chest or an abdomen of a patient, a harness mechanically linked to the cuirass and the backpack, and a seal mechanically linked to the border. The shell includes an interior face, an exterior face, and at least two ribs. The at least two ribs protruding from the exterior face of the shell. The harness provides a tension that pulls the cuirass towards the backpack.

In some embodiments, the cuirass further includes a pneumatic port. The pneumatic port is mechanically linked to a pneumatic tube. The pneumatic tube is mechanically linked to the pressure creation means. In some embodiments, the pneumatic port is located within one of the at least two ribs.

In some embodiments, the at least two ribs have a thickness of between 1.5 and 2.5 centimeters.

In some embodiments, the seal includes a first lip and a second lip. The first lip is located within an interior volume of the shell. The second lip is located externally to the interior volume of the shell.

In certain embodiments, provided herein is a method for manufacturing a cuirass, including scanning an anterior portion of at least one of a chest or an abdomen of a patient with a three-dimensional scanner, collecting data points representing a three dimensional model of the at least a portion of at least one of the chest or the abdomen of the patient, constructing a model of a cuirass comprising a shell, and manufacturing the cuirass through one of at least one of a vacuum forming process or a three-dimensional printing process. The shell includes a border shaped for engagement with the anterior portion of at least one of the chest or the abdomen of the patient. The vacuum forming process includes making a three-dimensional mold of the model of the cuirass and vacuum forming a material to the three-dimensional mold to produce the cuirass. The three-dimensional printing process includes producing the cuirass through the use of a three-dimensional printer.

In some embodiments, the method further includes collecting data points representing a three-dimensional model of at least one of the chest or the abdomen of the patient.

In some embodiments, the methods provided reduce dyspnea on exertion in a patient as a result of the use by a patient of a device of any of the above embodiments.

BRIEF DESCRIPTION OF THE DRAWINGS

FIG. 12A and FIG. 12B depict an exemplary docking stand for easily positioning the wearable portion on the patient.

DETAILED DESCRIPTION OF THE INVENTION

Figure 1:
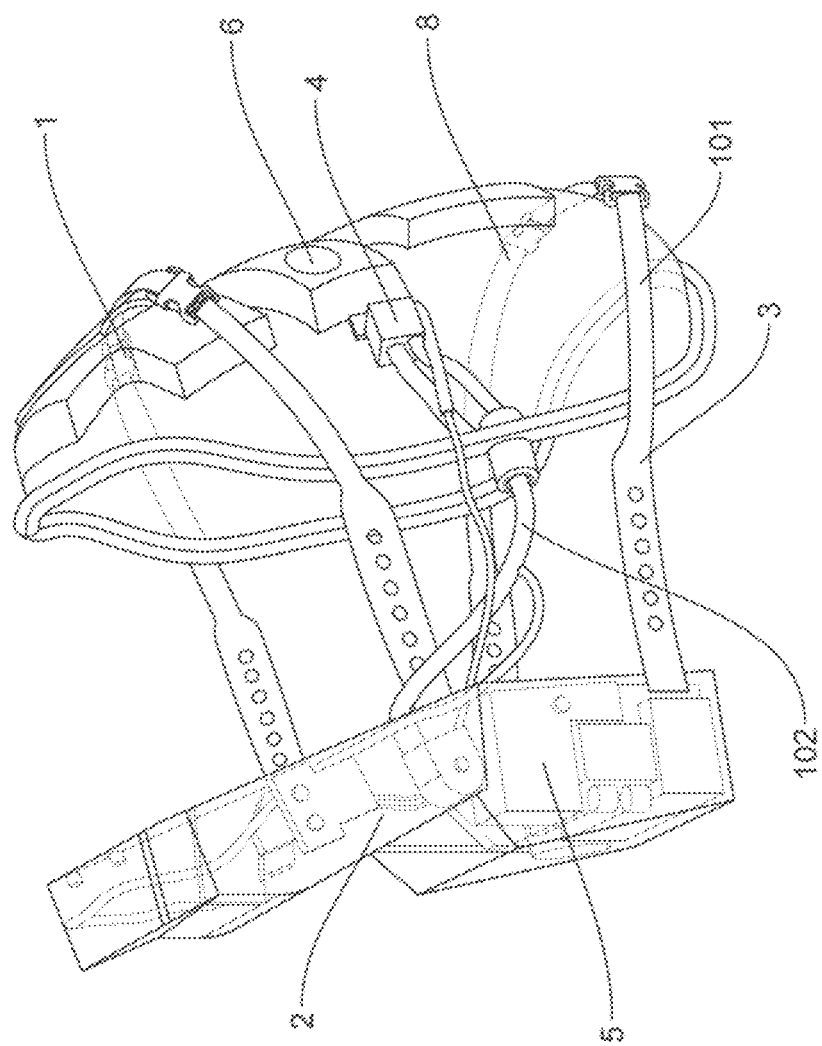
FIG. 1 depicts a side view of an exemplary cuirass, backpack, and harness.

Various terms relating to the methods and other aspects of the present disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "more than 2" as used herein is defined as any whole integer greater than the number two, e.g., 3, 4, or 5.

The term "plurality" as used herein is defined as any amount or number greater or more than 1. In some embodiments, the term "plurality" means 2, 3, 4, 5, 6 or more.

The terms "left", "right", "top", or "bottom" are used herein as a matter of mere convenience, and are determined by standing at the rear of the machine facing in its normal direction of travel. Likewise, "forward" and "rearward" are determined by the normal direction of travel. "Upward" and "downward" orientations are relative to the ground or operating surface as are any references to "horizontal" or "vertical" planes.

The term "about," "approximate," or "approximately" as used herein when referring to a measurable value such as an amount, a temporal duration, and the like, is meant to encompass variations of ±20%, ±10%, ±5%, ±1%, ±0.5%, ±0.4%, ±0.3%, ±0.2%, ±0.1%, ±0.09%, ±0.08%, ±0.07%, ±0.06%, ±0.05%, ±0.04%, ±0.03%, ±0.02% or ±0.01% from the specified value, as such variations are appropriate to perform the disclosed methods.

The term "substantially equal" as used herein when referring to a measurable and/or adjustable value is meant to encompass a value equal to or approximately equal to a set value or range. For example, the value can be equal to or within ±5%, ±1%, ±0.5%, ±0.4%, ±0.3%, ±0.2%, ±0.1%, ±0.09%, ±0.08%, ±0.07%, ±0.06%, ±0.05%, ±0.04%, ±0.03%, ±0.02% or ±0.01% of a set desired value or an expected value.

The term "connect", "connects", "connected", or "connecting" as used herein is meant to encompass both direct connections and indirect connections.

The terms "chest" or "abdomen" as used herein is meant to encompass the anterior portion of a human's chest or abdomen. The addition of the phrase "the anterior portion" as used herein is meant as clarification rather than to refer to a distinct portion of the chest or abdomen of the patient. The term "torso" as used herein refers to the portion of a human's body that includes the chest, abdomen, and back and may be used to refer any area within that portion of the body.

The term "interior volume" as used herein is meant to encompass the approximate volume of the space defined by the interior face of the cuirass and the surface of the body of the patient wearing the cuirass that is encircled by the border of the cuirass. If a patient is not wearing the cuirass, the interior volume may be approximated as the space defined by the interior face of the cuirass and a roughly flat plane projected across the border of the cuirass.

The term "interior face" as used herein is meant to encompass the side of the shell that, when the cuirass is worn by a patient so the border is pressed to the torso of the patient, is facing towards the torso of the patient. The term "exterior face" as used herein is meant to encompass the side of the shell that, when the cuirass is worn by a patient so the border is pressed to the torso of the patient, is facing away from the torso of the patient.

The term "negative pressure" as used herein is meant to encompass a pressure within the interior volume of a cuirass below the ambient pressure, this may also commonly be thought of as suction.

The term "positive pressure" as used herein is meant to encompass a pressure within the interior volume of a cuirass above the ambient pressure.

The term "cuirass" as used herein is meant to encompass a generally shell-shaped ventilator that fits over the anterior chest and/or the anterior abdomen, with space between the chest/abdomen and the shell that can be alternately pressurized and evacuated by a ventilator.

In some embodiments, the devices provided herein include a breathing mechanism sensing system for treating patients with breathing disorders such as COPD to assist in the patient's breathing by reducing the muscular effort and the energy required by a patient to inhale or exhale. This can be done by providing either a negative pressure, a positive pressure, or a combination of the two within the interior volume of a cuirass, when said cuirass is configured to the abdomen of a patient. The pressure assists the patient in breathing by either pushing in or pulling out the chest of the patient; a positive pressure within the interior volume pushes the chest of the patient inward to assist in exhalation and a negative pressure within the interior volume creates a suction force on the chest of the patient to assist in inhalation. The breathing mechanism sensing system allows the pressure created within the cuirass to be more efficient, effective, and comfortable for the patient by matching the pressure to the breathing pattern of the patient.

For example, FIG. 1 depicts a particular embodiment of the present disclosure comprising a cuirass 1. The cuirass 1 is connected via a harness 3 with straps 101 to a backpack 2. In some embodiments, the backpack 2 may be used to carry other elements of the device. In some embodiments, the backpack 2 may be made of the same material as the shell 8. In some embodiments, a pressure creation means 5 may be housed within the backpack 2 and connected via pneumatic tubes 102 to a pneumatic port 6 which is an opening in the shell 8 of the cuirass 1. In some embodiments, the pneumatic tubes 102 may be made of a flexible material to allow for greater freedom of motion for the patient. The pressure creation means 5 may be any device known to those in the art for creating a pressure in an enclosed space including, but not limited to, an air pump. Embodiments of the cuirass 1 and the different elements of the cuirass 1, such as the shell 8, are further discussed below and may further be seen in FIGS. 2, 4, 5, and 6.

The harness 3 may include the straps 101, which are used to provide a force pulling the cuirass 1 towards the backpack 2. A patient, or another person such as a doctor or assistant, may position the cuirass 1 to the chest, with the straps 101 extending from a portion of the cuirass 1 around the chest of the patient towards the back portion of the torso to connect to the backpack 2. By then tightening the straps 101, the cuirass 1 and backpack 2 remain in the desired position on the torso. Preferably, the device includes the cuirass 1 positioned on the chest or abdomen of a patient, straps 101 around each side of the torso, to a backpack 2 positioned on the back of the patient. An exemplary positioning of the cuirass 1 and the backpack 2 while being worn by a patient may further be seen in FIG. 8. This positioning allows the cuirass 1 to engage with the chest and to impart the necessary forces and or pressures onto to aid the patient with COPD to breathe easier.

Figure 2:
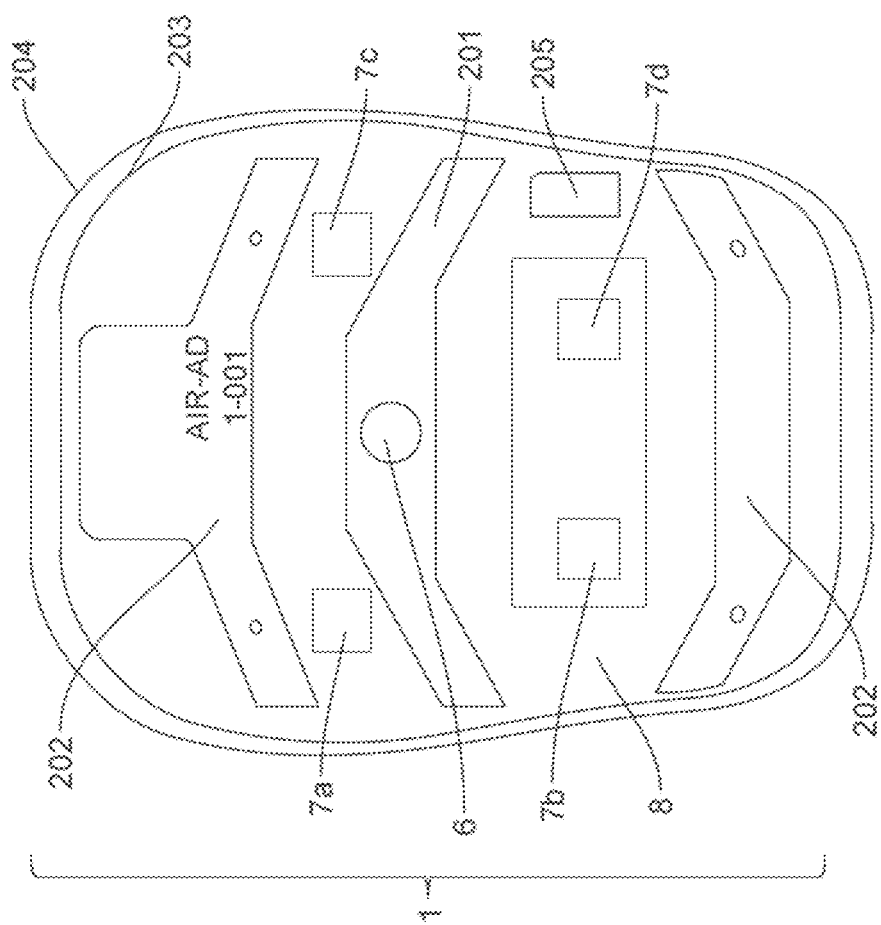
FIG. 2 depicts a top plan view of an exemplary cuirass.
Figure 6:
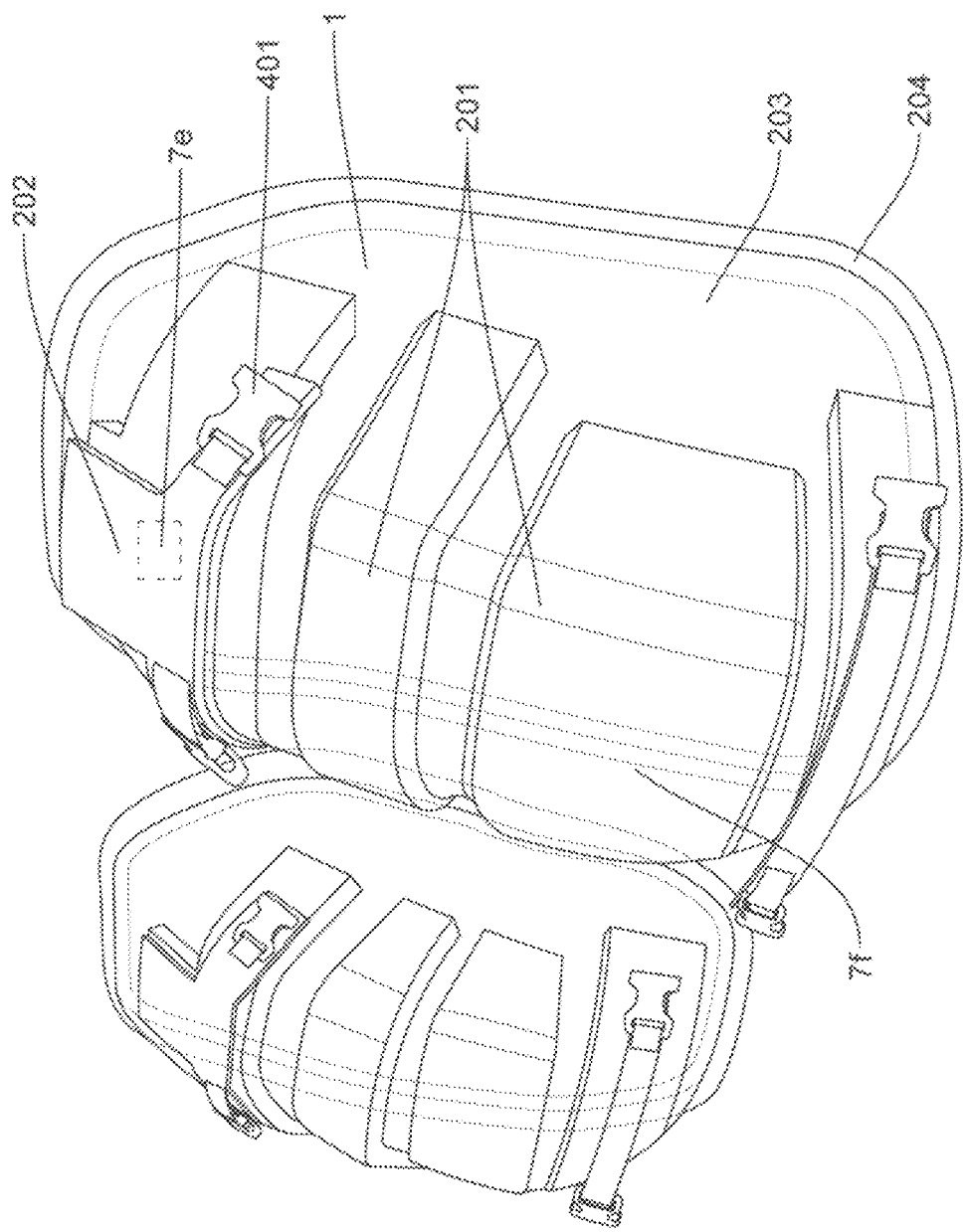
FIG. 6 depicts two exemplary cuirasses.

FIG. 2 shows a top plan view of the cuirass 1. In some embodiments, the cuirass 1 may include sensors 7a, 7b, 7c, and 7d. In some embodiments, there may be only one sensor 7a, 7b, 7c, or 7d. In some embodiments, there may any number of sensors 7a, 7b, 7c, and 7d, including, but not limited to, two, three, or four sensors 7a, 7b, 7c, or 7d, or a grouping of any of sensors 7a, 7b, 7c, and 7d arranged in a matrix. FIG. 6 shows one such arrangement in which there are two sensors 7e and 7f, each of which may be any of or a combination of sensors 7a, 7b, 7c, and 7d. In some embodiments, the sensors 7a, 7b, 7c, and 7d may be mounted on the interior or exterior face of the shell 8 of the cuirass 1. In some embodiments, any or all of the sensors 7a, 7b, 7c, and 7d may be at least partially mounted within the shell 8 itself. In some embodiments, a harness-based sensor 7e may be any or all of the sensors 7a, 7b, 7c, and 7d may be mounted to the harness 3. In some embodiments, a body-based sensor 7g may be any or all of the sensors 7a, 7b, 7c, and 7d may be mounted to the body of the patient using a device known to a person of the art, including but not limited to using an elastic strap wrapped around the torso of the patient.

In some embodiments, any or all of the sensors 7a, 7b, 7c, and 7d may be distance sensors as further discussed below. By measuring the distance from the sensor 7a, 7b, 7c, or 7d to a point on the body of a patient, such as the patient's abdomen or chest, wearing the cuirass 1, the breathing pattern of the patient may be determined. For example, the abdomen and chest of a patient expand and contract while the patient inhales and exhales. The expansions and/or contractions may be monitored by a distance sensor.

In some embodiments, any or all of the sensors 7a, 7b, 7c, and 7d may be used to measure a physical quantity of the harness 3, including force, stress, and strain, or any combination thereof within the harness 3. These physical quantities of the harness 3 may change over time in response to the patient inhaling and/or exhaling which in turn will cause a change in distance between the cuirass 1 and the backpack 2 or otherwise cause a change in the physical quantities within the harness 3.

In some embodiments, any or all of the sensors 7a, 7b, 7c, and 7d may be an airflow sensor adapted to measure the airflow within the pneumatic port 6.

In some embodiments, any or all of the sensors 7a, 7b, 7c, and 7d may be a pressure sensor.

In some embodiments, the sensor 7 may be an impedance plethysmography sensor, a microphone, an EMG sensor, or an ultrasound sensor.

In some embodiments, any or all of the sensors 7a, 7b, 7c, and 7d may be a volume sensor. A volume sensor may detect the change of the interior volume of the shell 8. A change in the interior volume may indicate that the patient's body has moved in such a way to indicate an inhalation or exhalation; for example, the interior volume may decrease during a patient's inhalation due to the patient's chest moving outwards.

In some embodiments, the volume sensor may be a capacitive sensor including at least two electrodes: at least one of the electrodes being a body-based sensor worn by the patient and at least one of the electrodes being a cuirass-based sensor 7f being mounted to the cuirass 1. The cuirass-based sensor 7f may be any sensor 7a, 7b, 7c, or 7d, or any combinations thereof which are mechanically connected to the cuirass 1. Capacitive sensors are known in the art to be able to measure changes in distances between objects.

In some embodiments, the device described herein includes a capacitive sensor that is operably connected to a controller 4 capable of performing at least minimal computations or processing of data from input signals, where the change in distance between the electrodes that is detected by the capacitive sensor may be used to calculate the change in interior volume. In some embodiments, the volume sensor may be an airflow sensor. The airflow sensor may be used to measure the velocity of the air leaving or entering the cuirass 1 via the pneumatic port 6. When a physical dimension such as the length, diameter, circumference, or volume, or a combination thereof, of the pneumatic port is known, the approximate change of the interior volume may be calculated by a controller 4.

In some embodiments, a temperature sensor may be included within the interior volume, the pneumatic tube 102, or the pneumatic port 6 to calculate a more accurate change of the interior volume by using an ideal gas calculation.

The general construction of the above mentioned sensors is known to people skilled in the art, with the exception of the above-described capacitive sensor; the general construction of a capacitive sensor is known to people skilled in the art but the electrode placement and use in volumetric calculations is not. In some embodiments, any or all of the above sensors 7a, 7b, 7c, and 7d be the only sensor. In some embodiments, any combination of the above sensors 7a, 7b, 7c, and 7d may be used. In some embodiments, any or all of the sensors 7a, 7b, 7c, and 7d may be components of a single sensor. In some embodiments, any or all but one of the sensors 7a, 7b, 7c, and 7d may be a dummy sensor or a placeholder.

In some embodiments, the shell 8 may be made of a semirigid material, such as polycarbonate. In some embodiments, the shell 8 may be made of a transparent or semi-transparent material. Such a transparent or semi-transparent can be useful to the patient in many ways. One such use is that it allows optical sensors that are not mounted within the cuirass 1 to obtain measurements within the interior volume. Another such use is to provide the patient or a doctor the ability to observe the torso of the patient while the patient is wearing the device. In some embodiments, the shell 8 may be made of an opaque material. In some embodiments, the shell 8 may be made of an opaque material and include transparent or semi-transparent portions, referred to as windows.

In some embodiments, the shell 8 may include ribs 201 protruding from the exterior face of the shell 8. In some embodiments, these ribs 201 may be solid such that the interior face of the shell 8 is approximately flat between the portion of the interior face opposite the rib 201 and the portion of the interior face opposite the exterior face without a rib 201 adjacent to the rib 201. One advantage of a solid rib 201 is that it provides more strength to the cuirass 1.

In some embodiments, the ribs 201 may be hollow, such that the interior face opposite the rib 201 is further from a patient's body than the portion of the interior face adjacent without a rib 201 that is adjacent to the rib 201. One advantage of a hollow rib 201 is that it may allow for additional components to be mounted within the interior volume. Another advantage of a hollow rib is that it may weigh less than a solid rib. In some embodiments, the pneumatic port 6 may be located within one of the ribs 201.

In some embodiments, the ribs 201 may be a varying width and/or height. The height of a rib 201 meaning the distance the rib 201 protrudes from the exterior face of the shell 8. In some embodiments, the ribs 201 may be of a uniform width and/or height. In some embodiments, the ribs 201 may be between approximately 1.0 cm and 5.0 cm in height. Such a range allows for increased strength of and, in some embodiments, interior volume within the cuirass 1 while limiting the weight and height of the cuirass 1, In some embodiments, the ribs 201 are approximately 2 cm in height; and in some embodiments, the ribs 201 are approximately 1.5 cm, 2.0 cm, 2.5 cm, or any number within the range of 1.5 to 2.5 cm in height.

In some embodiments, the cuirass 1 may include at least one plate 202. In some embodiments, the plate 202 may be constructed of a rigid material or metal. In some embodiments, the plate 202 may provide additional support and strength to the cuirass. In some embodiments, the harness 3 may include multiple plates 202 of the same or different shapes and sizes. In some embodiments, any or all of the sensors 7a, 7b, 7c, and 7d may be mounted on the plates 202.

Any or all of the sensors 7a, 7b, 7c, and 7d are operably connected to the controller 4 and sends an input signal to the controller 4 corresponding to the parameters sensed by any or all of the sensors 7a, 7b, 7c, and 7d. In some embodiments, the connection between any or all of the sensors 7a, 7b, 7c, and 7d and controller 4 may be by wire. In some embodiments, the connection between any or all of the sensors 7a, 7b, 7c, and 7d and controller 4 may be wireless, such as by Bluetooth signal. The controller 4 receives the input signal from any or all of the sensors 7a, 7b, 7c, and 7d and sends an output signal to the pressure creation means 5 which causes the pressure creation means 5 to provide a greater or lesser amount of pressure within the interior volume of the cuirass 1. In some embodiments, the greater or lesser amount of pressure may refer to the amplitude of positive pressure. In some embodiments, the greater or lesser amount of pressure may refer to the amplitude of negative pressure. In some embodiments, the greater or lesser amount of pressure may refer to the amplitude of both positive and negative pressure.

In some embodiments, the device described herein includes a human interface which includes the way that the patient interacts with the device, for example, by inhaling or exhaling to interact with any or all of the sensors 7a, 7b, 7c, and 7d. In some embodiments, the human interface may include a manual interface 205. In some embodiments, the manual interface 205 may be a dial or a set of dials. In some embodiments, the manual interface 205 allows the patient to modify the maximum pressure level, which is the amplitude of the negative and/or positive pressure. In some embodiments, the manual interface 205 allows the patient to manually modify the maximum rate of change over time of the pressure within the interior volume, also known as the pneumatic curves. In some embodiments, the manual interface 205 allows the patient to modify both the amplitude of the negative and/or positive pressure and the pneumatic curves. Such a manual interface 205 allows patients to modify the device to be more effective or more comfortable. In some embodiments, the manual interface 205 would not allow a patient to increase the amplitude of the negative and/or positive pressure or the pneumatic curves above or below preset thresholds, including but not limited to, safety thresholds.

Figure 3:
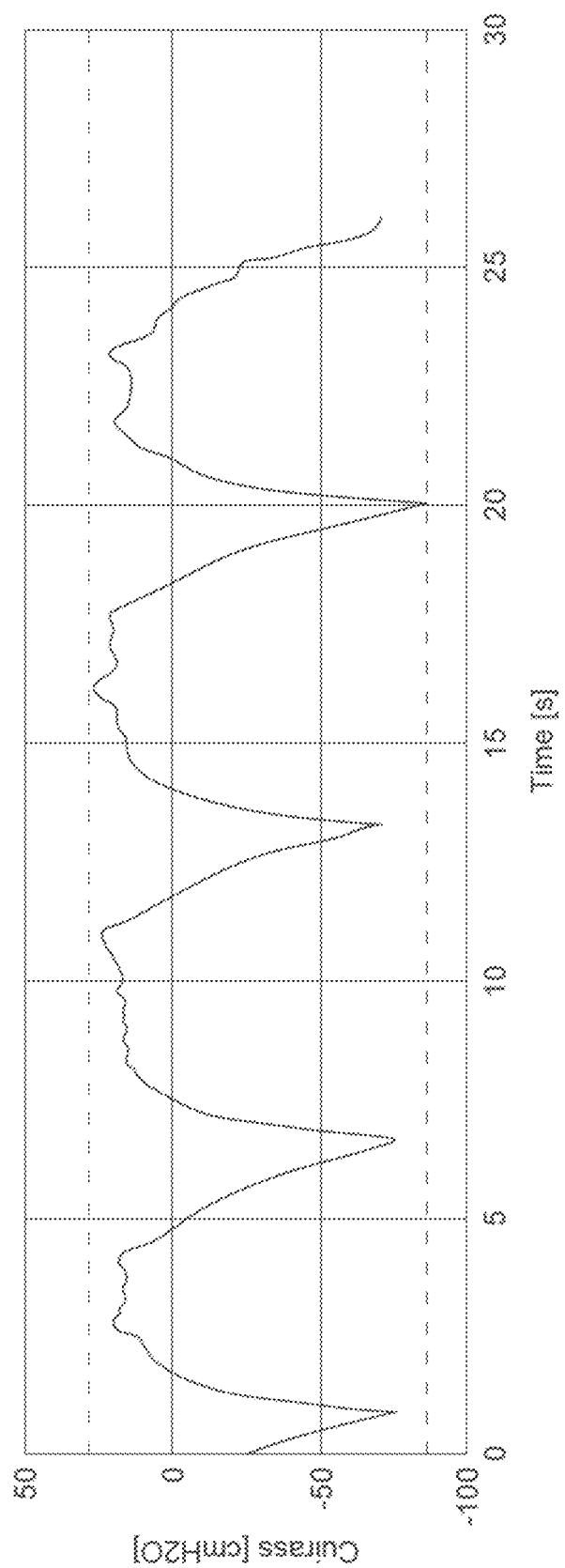
FIG. 3 depicts a chart of the pressure within the interior volume of an exemplary cuirass over a time period in which both positive and negative pressure is being created by a pressure creation means.

FIG. 3 shows a chart of pressure within the cuirass 1 over time while the pressure creation means 5 is operating. In some embodiments, the breathing mechanism sensing system can use at least one sensor 7a, 7b, 7c, or 7d operably linked to a controller 4 to monitor and control the wavelength, amplitude, or other characteristics of the pressure within the cuirass 1 that is controlled by the pressure creation means 5. The wavelength may require alteration to better match the breathing pattern of a patient. The wavelength may be considered as either the time between inhalations or exhalations of a patient wearing the cuirass 1. In some embodiments, a device provided herein may assist in either the inhalation or exhalation of the patient wearing the cuirass, or with both inhalation and exhalation. This assistance would be provided by the pressure creation means 5 creating a negative pressure to assist the patient in inhaling or a positive pressure to assist the patient in exhaling.

In some embodiments, a device provided herein may assist in both the inhalation and exhalation of the patient wearing the cuirass 1. In view of FIG. 3, the amplitude corresponds to the amount of pressure within the cuirass 1. The amplitude may require alteration to allow the device to be more effective: the higher the amplitude, the more negative pressure and/or positive pressure is being exerted by the pressure creation means and the more pressure being exerted, the less muscular effort the patient will need to exert to breath. However, the ideal amplitude is not the maximum available to a pressure creation means. This is because higher pressures may cause discomfort or even pain for the patient. In one experiment, it was found that a positive pressure of approximately 70 cmH2O caused pain in a patient wearing the cuirass 1. However, the precise amount of pressure required for each patient and the disease state of the patient is highly variable. Certain patients may require greater pressure to breathe, while other patients may require a much lower pressure to breathe. Similarly, certain patients may find discomfort at lower or greater pressures than another. Thus, the precise ranges for use are highly dependent on the individual, but a pressure typically falls within about 0 to 100 cmH2O for positive pressure and between −100 and 0 cmH2O for negative pressure, inclusive of all pressures within these range (−100 to 100 cmH2O).

In some embodiments, these characteristics may be altered by stopping or starting the pressure creation means 5. In some embodiments, these characteristics may be altered by increasing or decreasing the flowrate of a pump which is used within the pressure creation means 5. The rate of change over time of the pressure within the cuirass 1, also known as the pneumatic curves, can have an impact on patient comfort as well. In some embodiments, a maximum slope of the pneumatic curves may be set to prevent uncomfortable transitions from a negative pressure to a positive or neutral pressure or from positive pressure to a negative or neutral pressure. In some embodiments, the maximum slope of the pneumatic curves may be dependent on the flowrate of a pump used as a pressure creation means or on the rotations per minute (RPMs) of the pump.

For example, the wavelength of the pressure in FIG. 3 is approximately 6 seconds. The amplitude of the positive pressure is approximately 30 cmH2O. The amplitude of the negative pressure is approximately −80 cmH2O. In some embodiments, a refractory period may be set during which the controller 4 would recognize that the patient would not have moved from exhalation to inhalation or vice versa over such a short period. In some embodiments, this refractory period may be between 50 and 500 milliseconds.

Figure 4C:
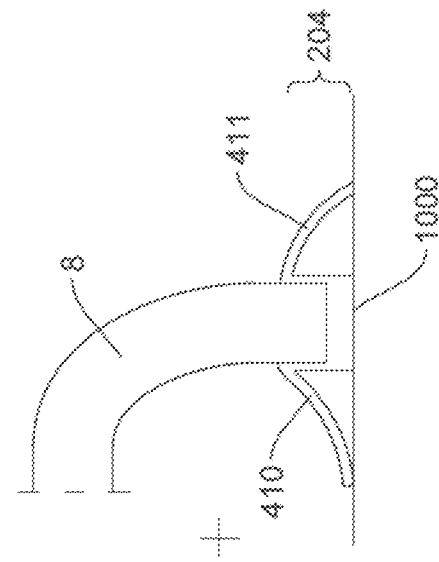
FIGS. 4A, 4B, and 4C depict an exemplary double-lipped seal when the interior volume of the cuirass has an ambient pressure, negative pressure, and positive pressure, respectively.
Figure 4A:
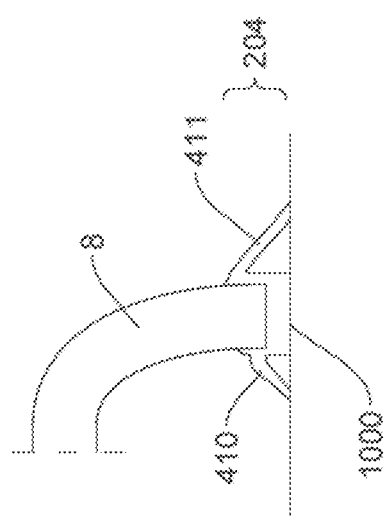
Figure 4B:
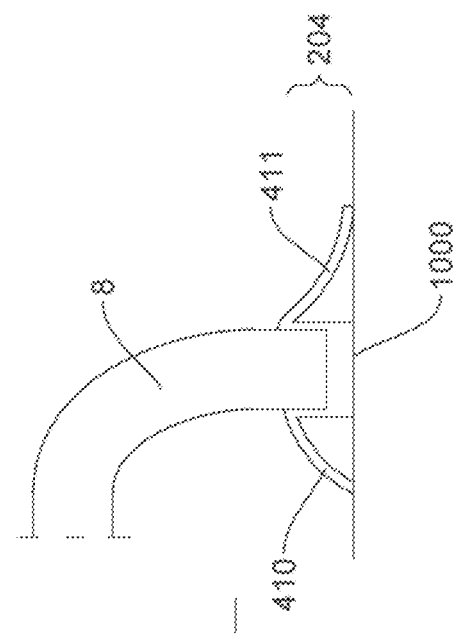
Figure 5:
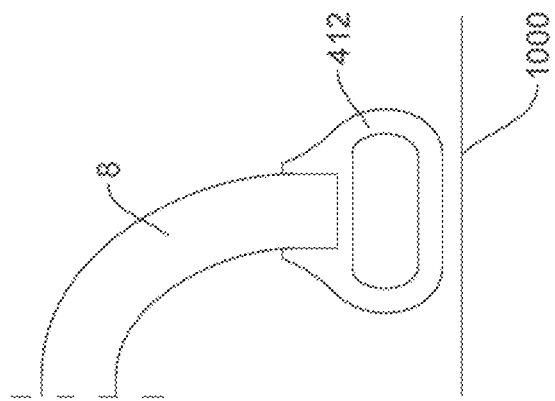
FIG. 5 depicts an exemplary large, hollow seal.
Figure 5:
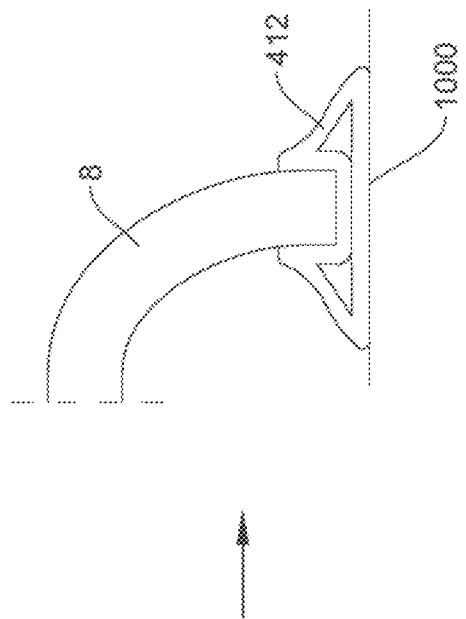

An important component of the devices described herein is a fundamental trade-off in the interior volume and the allowable leakage. While traditional cuirasses could have a larger size to achieve a greater volume in which pressure could be exerted, the devices provided herein are wearable cuirasses and there are therefore limitations on the dimensions of the cuirass 1 for the comfort and utility of the patient. Experiments have shown that as the interior volume of the cuirass 1 is decreased, the amount of leakage of air from or into the interior volume must be decreased to achieve effective pressure levels. In some embodiments, the limitations on the dimensions of the cuirass 1 may be imposed by the largest distance a patient is willing to have between the chest or the abdomen of the patient and the exterior face of cuirass 1, also referred to as the cuirass height. In some embodiments, limitations on the dimensions of the cuirass may be imposed by a desire to provide the patient with a full or approximately full range of motion in the patient's head, pelvis, arms, or a combination thereof. In some embodiments, a seal 204 may be mechanically connected to the border 203 of the shell 8 of the cuirass 1 through any commonly used seal connection method, including but not limited to using an adhesive such as glue, or other mechanical fastening device. In some embodiments, the seal 204 may be a double-lipped seal and pressed against the patient's torso 1000, with one lip being located on the side of the seal facing the interior volume of the cuirass, referred to as the interior lip 410, and the second lip being located on the opposite side of the seal, referred to as the exterior lip 411, as seen in FIG. 4A. Such a double-lipped seal is limits leakage by engaging one lip when positive pressure is exerted and the other when negative pressure is exerted. When negative pressure is exerted as seen in FIG. 4B, the double lipped seal is pulled inward towards the interior volume of the cuirass and the exterior lip 411 of the seal is engaged. When positive pressure is exerted as seen in FIG. 4C, the seal is pushed outwards away from the interior volume of the cuirass and the interior lip 410 of the seal is engaged. In some embodiments, a seal with a hollow interior 412 may be used in place of the double-lip seal to emulate the effects of the double-lip seal as seen in FIG. 5. This requires that the hollow interior and the exterior size of the seal 412 be sufficiently large that two essentially separate hollow interior areas are formed when the border 203 of the shell 8 is in engagement against the body 1000 of the patient.

In some embodiments, the border 203 may be shaped for engagement with the torso of the patient. The closer that the border 203 mimics the curves of the patient's torso, the closer engagement can occur. If the border 203 exactly follows the curves of the patient's torso, the cuirass 1 can be fully engaged with the torso of the patient and there will be minimal leakage of air from or to the interior volume. In some embodiments, such closer engagement may be achieved by using a three-dimensional scanner as described below. In some embodiments, the border may be an approximation of the curves of the patient's torso.

FIG. 6 provides a perspective view of two exemplary cuirasses. In FIG. 6, the plates 202 are used as the connection point between the harness 3 and the cuirass 1. The plates 202 are mechanically linked to the shell 8. Fasteners 401 are mechanically linked to the plates 202. The at least one of the fasteners 401 is adapted to receive the straps 101. In some embodiments, the fasteners 401 may be ratchet fasteners, which may receive and engage the straps 101 and then be manually operated to shorten the distance between the cuirass 1 and the backpack 2. The harness 3 provides a tension that pulls the cuirass 1 towards the backpack 2. When the cuirass 1 and the backpack 2 are worn by a patient, the fasteners 401 may be used to shorten the length of the straps 101 and cause the harness 3 to provide the requisite tension that will allow the cuirass 1 and backpack 2 to stay in place on the torso of the patient.

Figure 7:
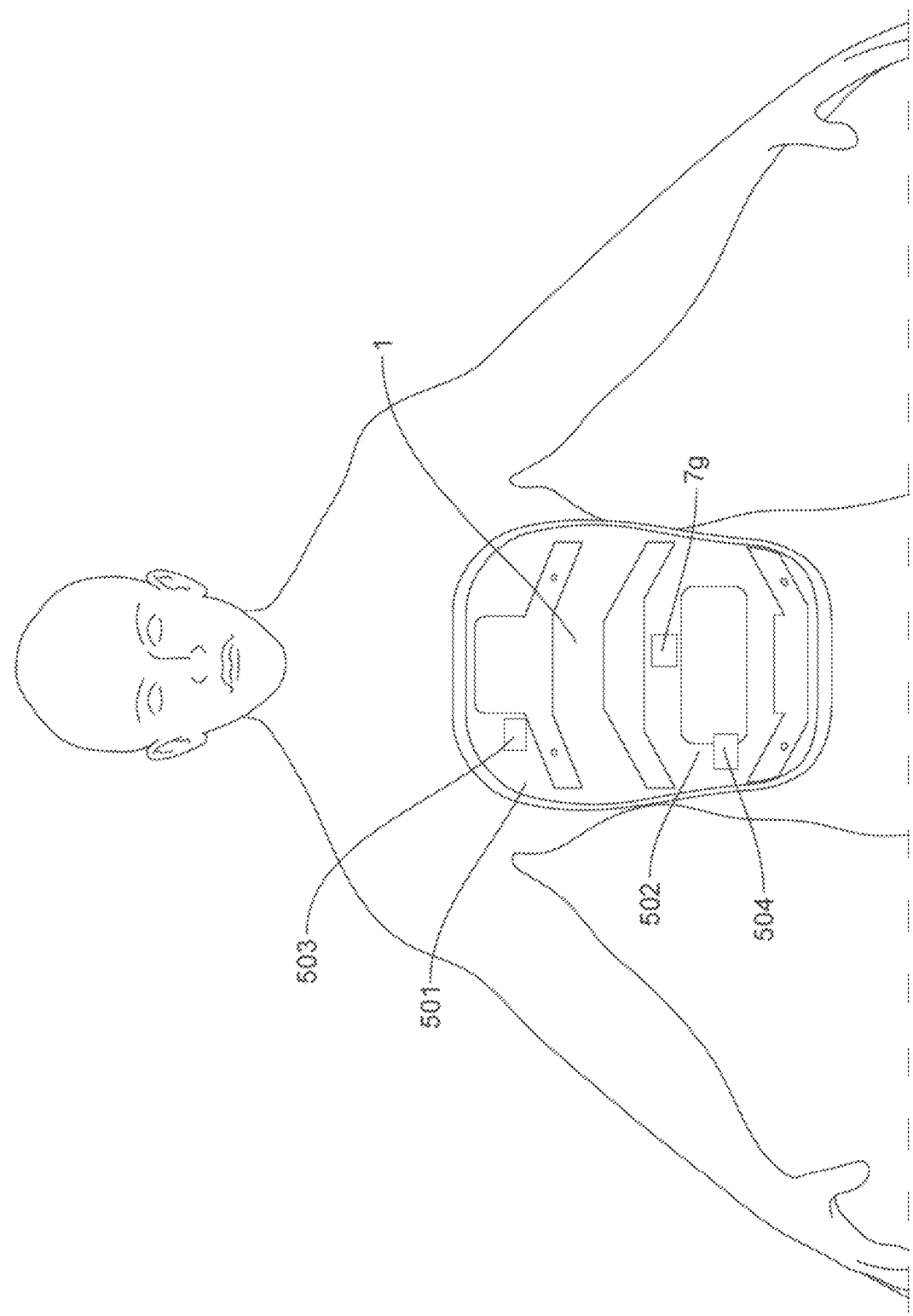
FIG. 7 depicts an exemplary cuirass positioned upon the torso of the patient.

FIG. 7 shows a patient wearing a cuirass 1 on the abdomen of the patient. In the embodiment shown in FIG. 7, the device includes at least two sensors 503 and 504 adapted to measure distance. Sensors 503 and 504 may be any of or any combination of sensors 7a, 7b, 7c, and 7d. At least one of the sensors 503 is positioned to measure the distance between the cuirass 1and the chest 501 of the patient. At least one of the sensors 504 is positioned to measure the distance between the cuirass 1 and the abdomen 502 of the patient. In some embodiments, only the sensor 503 may be present. In some embodiments, only the sensor 504 may be present. In some embodiments, the device includes two sensors 503 and two sensors 504, located approximately symmetrically to the right and left of the center of the shell 8. In some embodiments, the two sensors 503 are located closer to the left and right border 203 of the shell 8 than the center of the shell 8. In some embodiments, a t-shirt may be included in the device. The t-shirt includes at least a painted portion. In some embodiments, the painted portion may include a portion of the t-shirt that will be in contact with the seal 204. Such a painted portion allows for stronger engagement between the patient and the seal 204, decreasing the amount of air leakage. In some embodiments, the painted portion may include a portion over at least a portion of at least either the chest 501 or the abdomen 502. Such a painted portion allows for a more accurate reading of the distance by at least either sensor 503 or 504.

Figure 8:
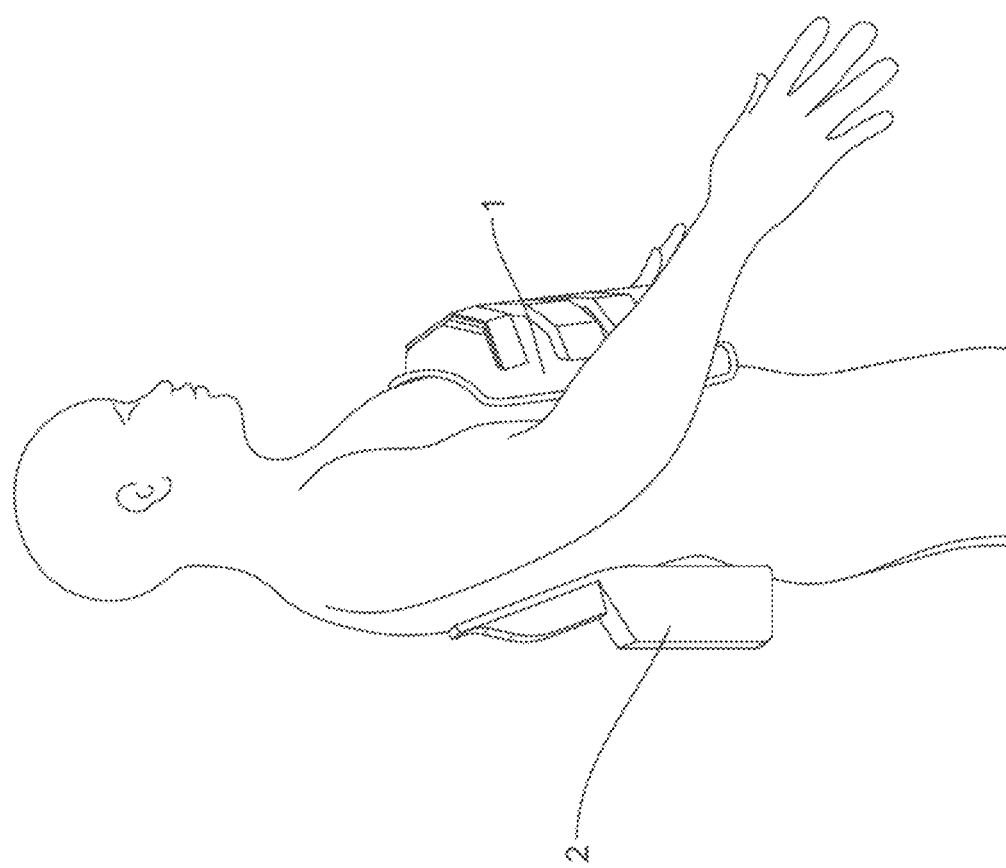
FIG. 8 depicts an exemplary cuirass and backpack positioned upon the torso of the patient.

FIG. 8 shows the preferred approximate positioning of the cuirass 1 and the backpack 2 in relation to a patient. While worn by the patient, the backpack 2 is positioned on the patient's back. In some embodiments, the backpack 2 may be shaped for engagement with the back of the patient, which may include, but is not limited to, having a wall which is shaped to approximately or completely mirror the curves of the patient's back, including, but not limited to, the patient's lower back. In some embodiments, the cuirass 1and the backpack 2 is arranged such that the center of gravity of the cuirass 1and the backpack 2 in combination is in the approximate same location as the center of gravity of the patient. In some embodiments, the pressure creation means 5 is located along the bottom portion of the backpack 2. Such an arrangement lowers the center of gravity of the device and increases the comfort and balance of the patient. In some embodiments, the height of the backpack 2, as measured from the side of the backpack 2 in contact with the patient to the opposing side of the backpack 2, is approximately equal to or less than 200 millimeters. In some embodiments, the height of the backpack 2 is approximately equal to or less than 40 centimeters. In some embodiments, the bottom side of the backpack 2 is not below the top of the gluteus maximus of the patient. In some embodiments, the bottom side of the backpack 2 is not below the bottom of the gluteus maximus of the patient. In some embodiments, the width of the backpack 2, as measured from the left to the right along the side of the backpack 2 in contact with the patient, is approximately equal to or less than the width of the patient's back.

Figure 9:
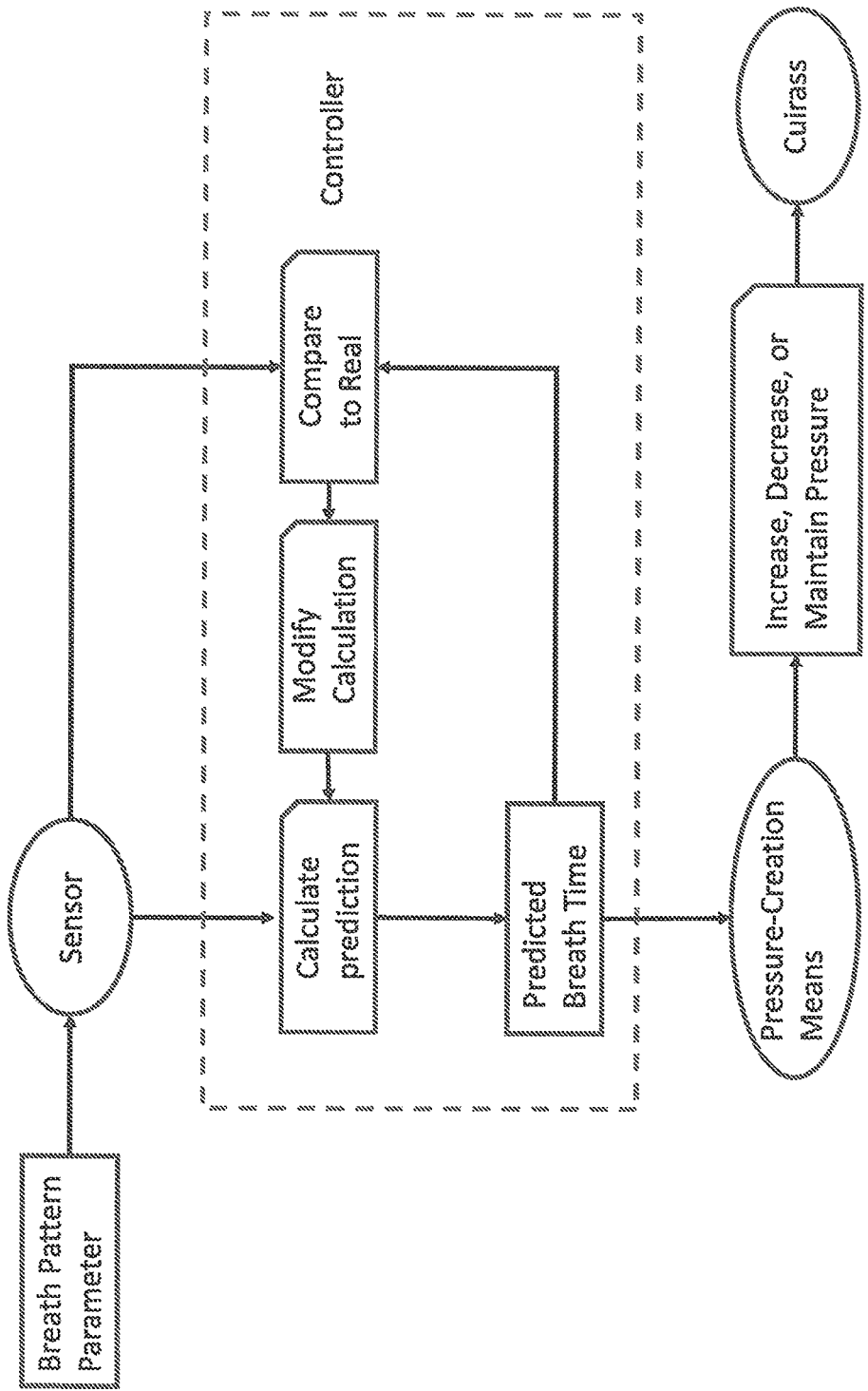
FIG. 9 depicts a flowchart of the process in which an exemplary embodiment may be calibrated.

FIG. 9 shows how the components of some embodiments of the device described herein may include a calibration system. This calibration system includes any or all of the sensors 7a, 7b, 7c, and 7d to measure a breath pattern parameter, using any or all of sensor 7a, 7b, 7c, and 7d or combination of sensors 7a, 7b, 7c, and 7d described herein that are capable of measuring the breath of a patient. The breath pattern parameter may be any measurable parameter that may vary as a patient inhales, exhales, pauses between inhalation and exhalation (or vice versa), or a combination of any of these actions. This parameter corresponds to the patient's breath pattern which may consist of the patient's inhalations, exhalations, pauses between inhalations and exhalations (or vice versa), or a combination of any of these actions. The controller 4 receives a breathing pattern input signal which is an input signal which may include data collected by the any or all of sensors 7a, 7b, 7c, and 7d in measuring the breath pattern parameter. The controller 4 monitors the collected data and calculates a predicted breath time of the patient. In some embodiments, the predicted breath time may be the time of a predicted future inhalation of the patient. In some embodiments, the predicted breath time may be the time of a predicted future exhalation of the patient. In some embodiments, the predicted breath time may be the time between the future inhalation and the future exhalation (or vice versa) of the patient.

In some embodiments, the predicted breath time may be the time of any predicted future stage of the breathing pattern of the patient. This predicted breath time is used by the controller 4 to calculate a wavelength for the pressure creation means 5 and to calculate when pressure corresponding to an inhalation and/or exhalation of the patient should be exerted by the pressure creation means 5. The controller 4 sends an output signal to the pressure creation means 5 to control the pressure within the cuirass 1 to correspond with the pressure characteristics calculated by the controller 4. The controller 4 can compare the predicted breathing pattern to the incoming breathing pattern signal from any or all of the sensors 7a, 7b, 7c, and 7d to monitor the accuracy of the predicted breathing pattern. There is some difference to be expected between actual and predicted breath patterns; however, a pre-determined threshold may be set in the controller 4 that if the difference is too great, the controller 4 may recognize the difference and modify the calculations used to create the predicted breath pattern to result in a more accurate prediction. In some embodiments, the calibration system may operate while the pressure creation means 5 is exerting or otherwise providing at least one of the negative pressure and the positive pressure. In some embodiments, the calibration system may operate while the provided pressure is constant. In some embodiments, the calibration system may operate while the provided pressure is varying. In some embodiments, the calibration system may operate while the pressure creation means 5 is not exerting or otherwise providing pressure. In some embodiments, the calibration system may include at least two stages: in the first stage, the pressure creation means 5 is exerting or otherwise providing at least one of either a positive pressure or a negative pressure and in the second stage, the pressure creation means 5 is not exerting or otherwise providing pressure. The first stage and the second stage are not restricted to any temporal order but the terms "first" and "second" are rather used to clarify the two distinct stages.

Figure 10:
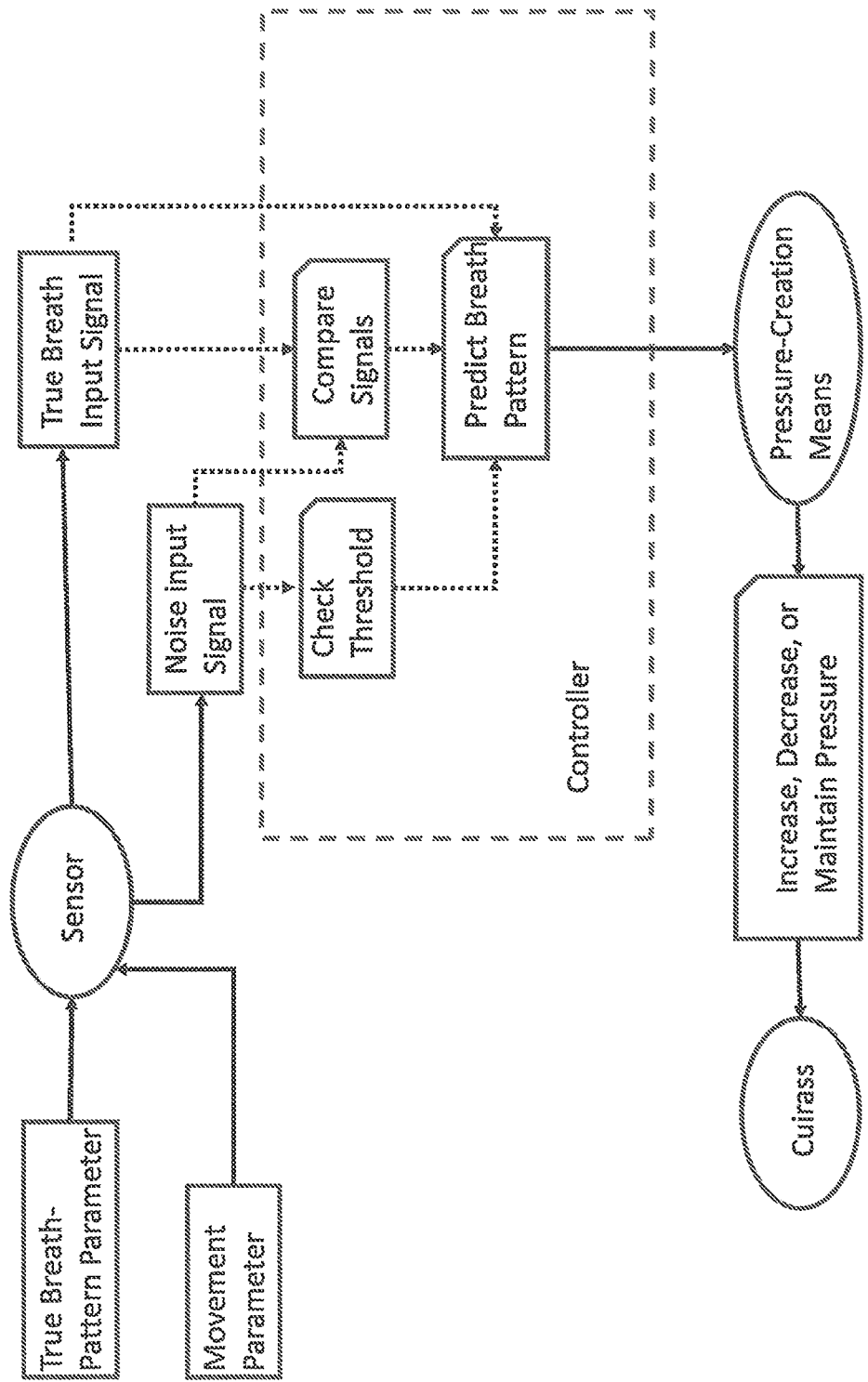
FIG. 10 depicts a flowchart of the process in which an exemplary embodiment may be used to remove motion artifacts.

FIG. 10 shows how the components of some embodiments of the device described herein may include a motion artifact removal system. This motion artifact removal system includes any or all of the sensors 7a, 7b, 7c, and 7d to measure a true breath pattern parameter and a movement parameter using any or all of the sensors 7a, 7b, 7c, and 7d or combination of sensors 7a, 7b, 7c, and 7d described herein that are capable of measuring the breath of a patient. The true breath pattern parameter may be any measurable parameter that may vary as a patient inhales, exhales, pauses between inhalation and exhalation (or vice versa), or a combination of any of these actions. The movement parameter may be any measurable parameter that varies in response to the movement of a patient's extremities, which may include any movement of the patient that is a movement made to inhale and/or exhale. In some embodiments, the same sensor 7a, 7b, 7c, or 7d may be used to measure the true breath-pattern parameter and the movement parameter. In some embodiments, a different sensor 7a, 7b, 7c, or 7d may be used to measure the true breath-pattern parameter than the sensor 7a, 7b, 7c, or 7d used to measure the movement parameter. Any or all of the sensors 7a, 7b, 7c, and 7d are operably connected to the controller 4 and provides the controller 4 with a true breath input signal which is an input signal which may include data collected by the any or all of sensors 7a, 7b, 7c, and 7d in measuring the true breath-pattern parameter and a noise input signal which is an input signal which may include data collected by the any or all of sensors 7a, 7b, 7c, and 7d in measuring the movement parameter.

In some embodiments, the controller 4 may compare the noise input signal to a pre-determined threshold. If the noise input signal is above the pre-determined threshold, then the controller 4 will modify way it processes the true breath input signal before sending an output signal based on the predicted breath pattern to the pressure creation means 5 to cause the pressure creation means 5 to modify or maintain the pressure within the cuirass 1. In some embodiments, the controller 4 may compare the true-breath signal to the noise input signal to determine whether to adjust a filter or other perform another modification to the true breath input signal before sending an output signal based on the predicted breath pattern to the pressure creation means 5 to cause the pressure creation means 5 to modify or maintain the pressure within the cuirass 1. In some embodiments, the controller 4 may do a combination of the above.

In some embodiments, the sensor 7a, 7b, 7c, or 7d that measures the movement parameter may be located exterior to the shell 8. In some embodiments, the sensor 7a, 7b, 7c, or 7d that measures the movement parameter may be located within or otherwise connected to the backpack 2. In some embodiments, the sensor 7a, 7b, 7c, or 7d that measures the movement parameter may be an accelerometer. In some embodiments, any or all of the sensors 7a, 7b, 7c, and 7d may a pressure sensor at least partially located within the interior volume and adapted to send the controller 4 a signal which may be used to calculate a pressure quality of the interior volume, including the pressure gradient, pressure amplitude, pressure signal shape, and pressure signal frequency or a combination thereof.

Figure 11:
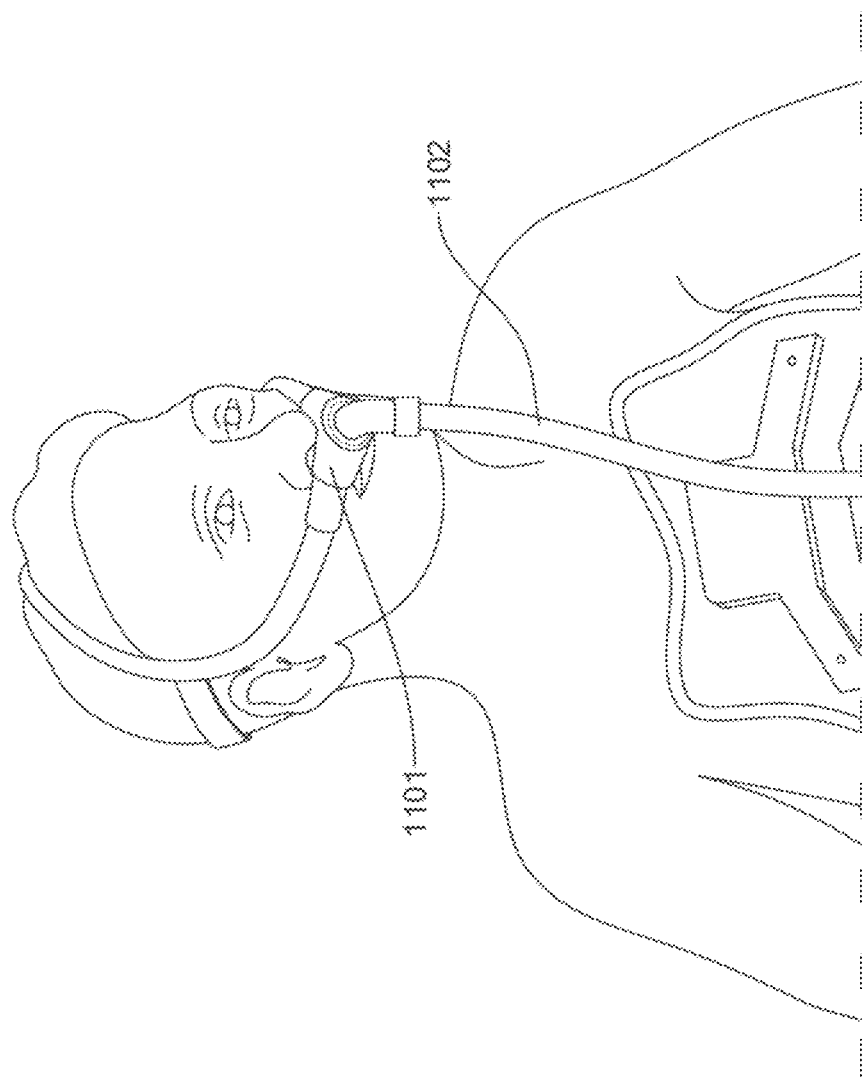
FIG. 11 depicts an exemplary mouth ventilator.

In some embodiments, the cuirass 1 could be used in combination with a mouth ventilator 1101 which is a ventilator adapted to be worn over a patient's mouth or nose, a non-limiting example is a CPAP device. In FIG. 11, the mouth ventilator 1101 may be connected to a ventilator pressure creation means by a mouth ventilator pneumatic tube 1102. In such an embodiment, the pressure provided to the cuirass 1and the mouth ventilator 1101 may provide a synergistic effect by providing a positive pressure to the mouth ventilator 1101 at the same or approximately same time that a negative pressure is exerted within the cuirass 1 to assist the patient in inhaling and/or providing a negative pressure to the mouth ventilator 1101 at the same or approximately same time as positive pressure is exerted within the cuirass 1 to assist the patient in exhaling. In some embodiments, the pressure creation means 5 which creates pressure within the interior volume of the cuirass 1 may be used as a ventilator pressure creation means as well. In some embodiments, the ventilator pressure creation means may be separate from the pressure creation means 5. The ventilator pressure creation means may be any device known to those in the art for creating a pressure in an enclosed space including, but not limited to, an air pump.

Figure 12A:
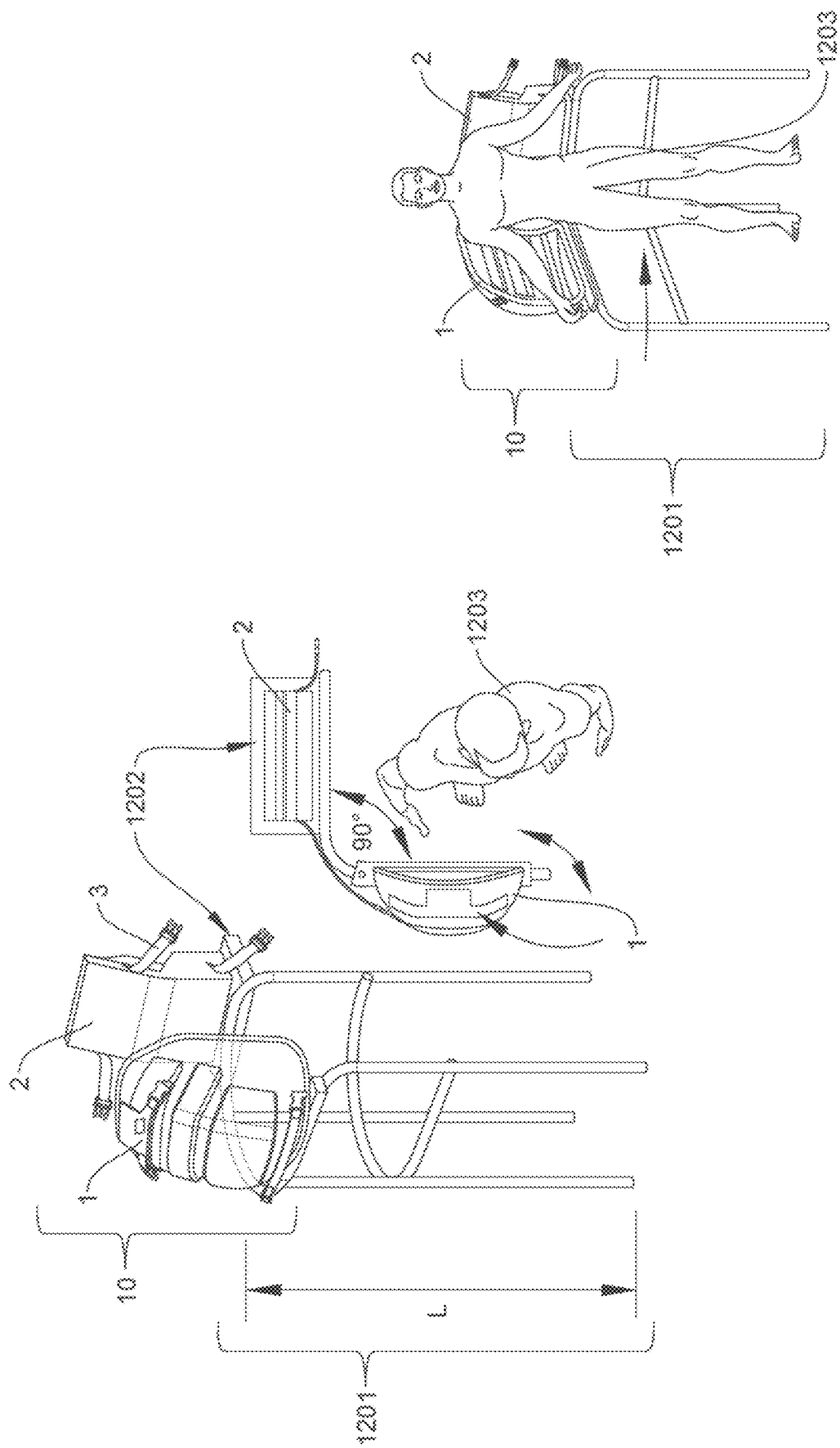

FIGS. 12A and 12B show an embodiment of the device that may include a docking stand 1201 to assist a patient 1203 in engaging and disengaging the cuirass 1, harness 3, and backpack 2, also referred to as the wearable portion 10 of the device. The docking stand 1201 may be at a height L appropriate for the patient 1203 to engage or disengage with the wearable portion 10 while standing or at a height appropriate for the patient to engage or disengage with the wearable portion 10 while sitting. Such a docking stand 1201 provides significant benefits in the comfort of the patient and the ease with which the device may be used. One reason for this is that the docking stand 1201 allows the patient 1203 to simply engage or disengage without the help of a second person. Another reason is that the docking stand 1201 allows the patient to expend less energy and use less muscles in engaging or disengaging, which is very important to a patient with COPD. The dock stand 1201 must engage either the cuirass 1, harness 3, or backpack 2 to be used for docking the wearable portion 10 of the device.

A docking catch mechanism is used to accomplish this engagement. This engagement could occur through any commonly known method for temporarily coupling or other mechanical linkage two objects, including but not limited to through a pin and catch system or through magnetic forces. In some embodiments, the backpack 2 may engage with a back shelf 1202 of the docking stand 1201. In some embodiments, the cuirass 1 may engage with a front shelf 1204 of the docking stand 1201. In some embodiments, the docking stand 1201 may be opened so the front shelf 1204 is at an approximately 90-degree angle from the back shelf 1202. When the docking stand 1201 is open, the patient 1203 may walk into the middle of the docking stand 1201. The patient 1203 may grasp the handles 1205 to better move the front shelf 1204 towards the back shelf 1202 to close the wearable portion 10 onto the torso of the patient 1203, thereby more easily positioning the wearable portion 10 on the patient's torso.

Figure 13:
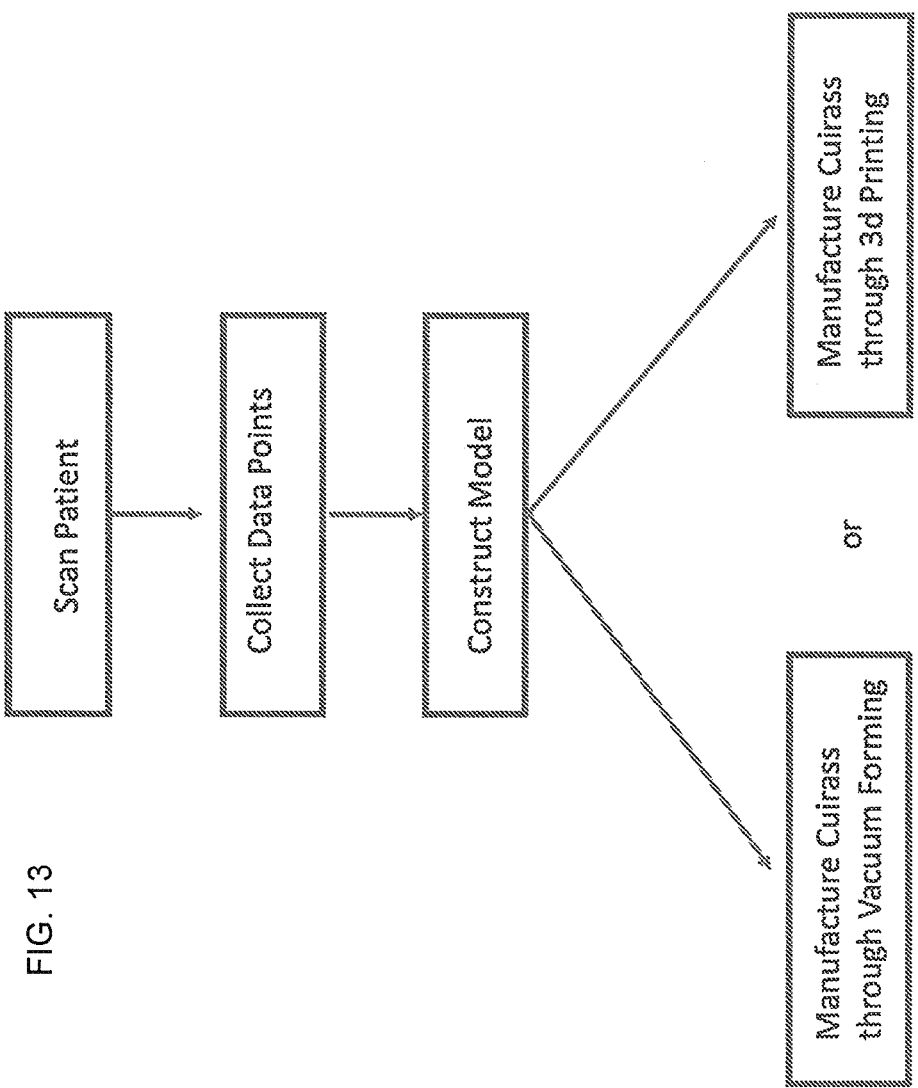
FIG. 13 depicts a flowchart of an exemplary method for creating a cuirass.

FIG. 13 shows a method for creating a cuirass 1. A cuirass 1 that is custom made for a patient allows for more effective engagement of the border 203 against the body of the patient. The method includes scanning an anterior portion of the patient's torso, for example at least one of a patient's chest 502 and abdomen 501. The scan may be made using any three-dimensional scanner known in the art. Data points are collected that represent a three-dimensional model of at least a portion of the portion of the patient's torso that was scanned. A model of the cuirass 1 including the shell 8 is then created such that the border 203 of the shell 8 is shaped for engagement with at least a portion of the portion of the patient's torso that was scanned. The cuirass 1 is then manufactured through either a vacuum forming process or a three-dimensional printing process. The vacuum forming process may be any such process that is known to a person skilled in the art, including, but not limited to, making a three dimensional mold of the model of the cuirass 1 and vacuum forming a material to the three-dimensional mold to produce the cuirass 1. In some embodiments, the mold may be manufactured using any CNC mill commonly known to a person skilled in the art. The three-dimensional printing process including producing the cuirass 1 of a material through the use of any three-dimensional printer commonly known to a person skilled in the art. In some embodiments, the material may be poly-carbonate. In some embodiments, the material may be any material commonly used to create a product or device in a vacuum forming process or three-dimensional printing process.

The ability to custom fit the cuirass 1 to fit a patient allows for a greater fit and comfort to the patient, but also allows for a tailored product, thus reducing air leaks. By reducing air leaks, and otherwise reducing bulk and imprecise fit, the complete size and weight of the product can be reduced, as compared to a generic sizing strategy. Furthermore, the reduction in air leaks allows for smaller pressure differentials to be utilizes, both positive and negative, to impart the necessary pressure to assist the patient with breathing.

An embodiment the device described herein further includes a method of reducing the dyspnea on exertion (DOE) in a patient, for example, in a patient with COPD, by using any of the above described devices or combinations thereof.

U.S. Provisional Patent Application No. 62/780,608, filed Dec. 17, 2018, and International Patent Application No. PCT/US2017/023326 are incorporated herein by reference in their entireties. Further, while the invention has been described with reference to particular embodiments, it will be appreciated that modifications can be made without departing from the spirit of the invention. Such modifications are intended to fall within the scope of the appended claims.

The invention claimed is:

1. A device comprising:
   a cuirass comprising a shell configured to be worn by a patient;
   a backpack shaped for engagement with an anterior portion of the back of the patient;
   a harness mechanically linked to the cuirass and the backpack, the harness providing a tension that pulls the cuirass toward the backpack;
   a cuirass pressure creation means for providing at least one of a negative pressure or a positive pressure within the shell, the cuirass pressure creation means included in the backpack;
   a controller operably connected to the cuirass pressure creation means; and
   at least one sensor adapted to measure a true breath pattern parameter corresponding to a patient's breathing pattern;
   wherein the controller is adapted to receive a breathing pattern input signal from the at least one sensor and to calculate a predicted breath time, the predicted breath time being a time at which at least one of a future inhalation or a future exhalation of the patient is expected to take place;
   wherein the controller is adapted to compare the breathing pattern input signal from the at least one sensor to the predicted breath time and to modify the predicted breath time if the breathing pattern input signal and the predicted breath time differ by a pre-determined threshold; and
   wherein the controller provides an output signal corresponding to the predicted breath time to the cuirass pressure creation means and the cuirass pressure creation means is adapted to provide a greater or lesser amount of pressure within the shell in response to the output signal.

2. The device according to claim 1, wherein the at least one sensor is adapted to measure a movement of an extremity of the patient, and wherein the controller is adapted to receive a noise input signal from the sensor corresponding to the movement of an extremity of the patient and to modify the breathing pattern input signal if the noise input signal meets or exceeds a pre-determined threshold.

3. The device according to claim 1, wherein the cuirass includes a pneumatic port that is mechanically linked to a pneumatic tube which is mechanically linked to the cuirass pressure creation means.

4. The device according to claim 3, wherein the shell is surrounded by a border shaped for engagement with an anterior portion of at least one of a chest or an abdomen of a patient, wherein the device includes a seal mechanically linked to the border, and wherein the shell comprises an interior face, an exterior face, and at least two ribs which protrude from the exterior face of the shell.

5. The device according to claim 4, wherein the pneumatic port is located within one of the at least two ribs.

6. The device according to claim 4, wherein the seal comprises a first lip and a second lip, the first lip being located within an interior volume of the shell and the second lip being located externally to the interior volume of the shell.

7. The device according to claim 1, further comprising a docking stand, wherein at least one of the cuirass, the harness, and the backpack comprises a docking catch mechanism, and wherein the docking catch mechanism is adapted to provide a temporary mechanical linkage between the docking stand and the at least one of the cuirass, the harness, and the backpack.

8. The device according to claim 1, wherein the at least one sensor includes a harness-based sensor mechanically linked to the harness.

9. The device according to claim 8, wherein the harness-based sensor comprises a first harness-based sensor and a second harness-based sensor, wherein the first harness-based sensor is adapted to measure the distance between the sensor and a patient's chest, wherein the second harness sensor is adapted to measure the distance between the sensor and a patient's abdomen, wherein the controller receives signals from the first harness-based sensor and the second harness-based sensor, and wherein the output signal of the controller is dependent upon the signals from the first harness-based sensor and the second harness-based sensor.

10. The device according to claim 8, wherein the harness-based sensor measures at least one of force, stress, and strain, or combinations thereof.

11. The device according to claim 1, wherein the at least one sensor includes a first cuirass-based sensor and a second cuirass-based sensor mechanically linked to the cuirass, wherein the first cuirass-based sensor measures a distance between the first cuirass-based sensor and a patient's chest and the second cuirass-based sensor measures a distance between the second cuirass-based sensor and a patient's abdomen, wherein signals from the first cuirass-based sensor and the second cuirass-based sensor are received as inputs by the controller, and wherein the output signal of the controller is dependent upon the signals from the first cuirass-based sensor and the second cuirass-based sensor.

12. The device according to claim 1, wherein the at least one sensor includes at least one of an airflow sensor, a pressure sensor, an impedance plethysmography sensor, a microphone, an electromyography (EMG) sensor, an ultrasound sensor, a volume sensor, a temperature sensor, and an accelerometer.

13. The device according to claim 1, wherein the at least one sensor includes a capacitive sensor comprising at least two electrodes, at least one of the electrodes being a body-based sensor and at least one of the sensors being a cuirass-based sensor, wherein the body-based sensor is adapted to be placed in direct or indirect contact with an anterior portion of at least one of the chest or abdomen of a patient and the cuirass-based sensor being in direct or indirect connection with the cuirass, wherein the controller is operably connected to the at least two electrodes and adapted to receive an input signal comprising at least a signal from the body-based sensor and a signal from the cuirass-based sensor, and wherein the controller is adapted to calculate an interior volume of the cuirass based on the input signal.

14. The device according to claim 1, wherein the cuirass comprises a pneumatic port mechanically linked to the cuirass pressure creation means, and the at least one sensor includes an airflow sensor adapted to measure airflow within the pneumatic port, wherein the controller is operably connected to the airflow sensor and is adapted to receive an input signal from the airflow sensor, wherein a physical dimension of at least a segment of the pneumatic port is known and is selected from the group consisting of length, diameter, circumference, volume, and combinations thereof, and wherein the controller is adapted calculate an interior volume of the cuirass based on the physical dimension and data received from the input signal.

15. The device according to claim 1, wherein the at least one sensor includes a pressure sensor and a temperature sensor, wherein the controller is operably connected to the pressure and temperature sensors and adapted to receive input signals from the pressure sensor and the temperature sensor, and wherein the controller is adapted to calculate an approximate volume of a space defined by an anterior portion of at least one of the chest or abdomen of the patient and the shell.

16. The device according to claim 1, wherein the shell comprises an interior face and an exterior face and the at least one sensor is a pressure sensor adapted to measure a movement parameter and being at least partially located within an interior volume of the cuirass, and wherein the controller is adapted to calculate a pressure quality selected from the group consisting of pressure gradient, pressure amplitude, pressure signal shape, pressure signal frequency, and combinations thereof, based on data received from an input signal provided by the pressure sensor.

17. The device according to claim 1, further comprising a manual interface adapted to allow a patient to manually modify at least one of a maximum pressure level within the cuirass or a maximum rate of change over time of pressure within the cuirass, wherein the controller is adapted to receive an input signal from the manual interface.

18. The device according to claim 1, further comprising a ventilator adapted to be worn over a patient's mouth, and a ventilator pressure creation means for providing at least one of a negative pressure or a positive pressure within the ventilator, wherein the controller is operably connected to the ventilator pressure creation means and provides positive pressure when the cuirass pressure creation means provides negative pressure.

* * * * *